(12) United States Patent
McClung

(10) Patent No.: US 6,579,543 B1
(45) Date of Patent: Jun. 17, 2003

(54) COMPOSITION FOR TOPICAL APPLICATION TO SKIN

(75) Inventor: Jackie H. McClung, 2700 NW. 19th St., Oklahoma City, OK (US) 73201

(73) Assignee: Jackie H. McClung, Oklahoma City, OK (US)

( * ) Notice: Subject to any disclaimer, the term of this patent is extended or adjusted under 35 U.S.C. 154(b) by 0 days.

(21) Appl. No.: 10/153,057

(22) Filed: May 21, 2002

Related U.S. Application Data

(63) Continuation of application No. 10/082,566, filed on Feb. 22, 2002, now abandoned.

(51) Int. Cl.[7] .......................... A61K 35/78; A61K 6/00; A61K 7/00; A01N 25/00
(52) U.S. Cl. ................ 424/728; 424/725; 424/729; 424/730; 424/734; 424/735; 424/401; 514/887; 514/817
(58) Field of Search ................. 424/401, 725, 424/728, 729, 730, 734, 735; 514/887, 817

(56) References Cited

U.S. PATENT DOCUMENTS

| | | | | |
|---|---|---|---|---|
| 5,431,924 A | * | 7/1995 | Ghosh et al. | 424/522 |
| 5,472,713 A | * | 12/1995 | Fein et al. | 424/522 |
| 6,004,566 A | * | 12/1999 | Friedman et al. | 424/400 |
| 6,416,772 B1 | | 7/2002 | Van Engelen et al. | |

* cited by examiner

*Primary Examiner*—Thurman K. Page
*Assistant Examiner*—Humera N. Sheikh
(74) *Attorney, Agent, or Firm*—Crowe & Dunlevy, P.C.

(57) ABSTRACT

A composition for topical application to an animal's skin for relief from a variety of symptoms caused by medical conditions or physical injuries. The composition includes at least one compound having analgesic activity, at least one compound having anti-inflammatory activity, at least one compound having antioxidant activity, at least one compound having anti-neuralgic activity, at least one compound having blood circulation promotion activity, and at least one compound having antidepressant activity. A method for relieving pain by topical application of the composition is also provided.

12 Claims, No Drawings

COMPOSITION FOR TOPICAL APPLICATION TO SKIN

CROSS REFERENCE TO RELATED APPLICATIONS

This application is a continuation of U.S. Ser. No. 10/082,566, filed Feb. 22, 2002 now abandoned, entitled "COMPOSITION FOR TOPICAL APPLICATION TO SKIN".

BACKGROUND OF THE INVENTION

1. Field of the Invention

The present invention relates generally to compositions for topical application to an animal's skin, and more particularly, but not by way of limitation, to compositions having analgesic activity for topical application to an animal's skin.

2. Brief Description of the Art

There presently exists a number of natural substances that are known to have analgesic and anti-inflammatory properties, including aloe vera, MSM, menthol, Coriander oil, herbal extracts such as arnica, willow bark, witch hazel and feverfew, and the like.

To have a substantial effect when applied topically, however, these substances must penetrate the skin adequately and be delivered to the point of pain or discomfort in an adequate fashion. This currently requires that such substances be applied to the skin very frequently and in large quantities. In addition, while such substances may demonstrate high potency when examined in vitro or in a laboratory model, relief of the signs and symptoms of pain and/or inflammation in a human subject may be less than desired because of the lack of an effective delivery system for reaching the tissue from which the pain and/or inflammation are originating.

Therefore, the present invention seeks to overcome the disadvantages and defects of the prior art by combining MSM with emu oil and a variety of medicinally active herbal extracts to provide effective relief from the pain and discomfort caused by a variety of medical conditions and physical injuries.

SUMMARY OF THE INVENTION

According to the present invention, a composition for topical application to an animal's skin is provided. Broadly, such composition comprises at least one compound having analgesic activity, at least one compound having anti-inflammatory activity, at least one compound having antioxidant activity, at least one compound having anti-neuralgic activity, at least one compound having blood circulation promotion activity and at least one compound having anti-depressant activity.

An object of the present invention is to provide a composition for topical application to an animal's skin.

Another object of the present invention, while achieving the before-stated object, is to provide a composition for topical application to an animal's skin for relief of pain and discomfort caused by a medical condition or a physical injury.

Another object of the present invention, while achieving the before-stated objects, is to provide a method for applying such compositions to an animal's skin.

Other objects, features and advantages of the present invention will become apparent from the following detailed description when read in conjunction with the accompanying drawings and appended claims.

DETAILED DESCRIPTION OF THE INVENTION

Before explaining at least one embodiment of the invention in detail by way of exemplary tables, experimentation, results, and laboratory procedures, it is to be understood that the invention is not limited in its application to the details of construction and the arrangement of the components set forth in the following description or illustrated in the tables, experimentation and/or results. The invention is capable of other embodiments or of being practiced or carried out in various ways. Also, it is to be under stood that the phraseology and terminology employed herein is for the purpose of description and should not be regarded as limiting.

The present invention is directed to a composition having analgesic, anti-inflammatory, antioxidant, anti-neuralgic, blood circulation promotion and antidepressant activities for topical application to an animal's skin. Preferably, the animal is a human; however, the composition of the present invention may also be applied topically to domesticated animals, such as but not limited to, dogs, cats, horses and the like. In addition, the composition for topical application to an animal's skin may be in the form of a lotion, a cream or a gel.

The composition of the present invention may be applied topically to a subject for relief of pain, discomfort and other symptoms associated with osteo, degenerative and rheumatoid arthritis; fibromyalgia; neuropathy; sciatica; cerebral palsy; lower back pain; sore muscles, including muscle cramps and muscle spasms; auto accident injuries; knee, hip, shoulder and hand pain; sports injuries, strains and sprains; musculoskeletal injuries; post surgery pain; shingles; menstrual cramps; sinus and migraine headaches; asthma; poison ivy; insect stings, such as bee, wasp and ant stings; insect bites, such as spider bites; ear and toothaches; burns, including sunburn; nerve damage pain from diseases such as diabetes; and other like conditions or injuries that cause a subject discomfort.

The composition of the present invention includes an effective amount of at least one compound having soothing, analgesic effects to provide relief from at least one of pain, soreness and discomfort. The analgesic compound is selected from the group consisting of aloe vera, MSM, emu oil, menthol, glucosamine, chondroitin, a capsaicinoid, arnica extract, coriander oil, Roman chamomile oil, willow bark extract, feverfew extract, St. John's wort extract, kava kava extract, nettle leaf, acetylsalicylic acid, Bala, black cohosh, black snakeroot, bugbane, squawroot, bupleurum, calendula, camphor, cayenne, devil's claw root, evening primrose oil, ginger, gotu kola, gingkgo, juniper, lavender oil, licorice, marjoram, meadow sweet, passion flower, quercetin, salicinum, wild yam, wintergreen, wood betony, wormwood and combinations thereof.

The composition further includes an effective amount of at least one compound having anti-inflammatory effects to provide relief from at least one of swelling, redness, fever and inflammation. The anti-inflammatory compound is selected from the group consisting of aloe vera, MSM, emu oil, chondroitin, glucosamine, a capsaicinoid, arnica extract, grape seed extract, coriander oil, marigold extract, nettle leaf extract, Roman chamomile oil, blue-bottle extract, St. John's wort, willow bark extract, witch hazel extract, feverfew extract, barley grass, black cohosh, black snakeroot, bugbane, squawroot, Boswellia, borage, bromelain, burdock, calendula, cayenne, dandelion, devil's claw root, DHEA (dehydroepiandosterone), Echinacea, EFAs (essential fatty acids such as omega-3 and omega-6 fatty acids including linoleic acid (LA) and alpha linolenic acid (LNA)), elderflower, evening primrose oil, flaxseed, ginkgo, ginger, ginseng, Hawthorne, kaempferol, licorice, life root, golden Senecio, squaw weed, golden groundsel, cocash weed, coughweed, ragwort, golden ragwort, grundy swallow, linden, marjoram, meadow sweet, NDGA, neem, Padma 28, quercetin, turmeric, wild yam, wormwood, yucca and combinations thereof.

The composition further includes an effective amount of at least one compound having antineuralgic effects to provide relief of pain or discomfort along a course of a nerve or in an area of distribution of the nerve. The antineuralgic compound is selected from the group consisting of a capsaicinoid, Roman chamomile oil, coriander oil and combinations thereof.

The composition further includes an effective amount of at least one compound having antioxidant activity to prevent damage or deterioration of tissue. The antioxidant compound is selected from the group consisting of chondroitin, vitamin C, grape seed extract, St. John's wort extract, coriander oil, barley grass, bilberry, Echinacea, garlic, ginger, ginkgo, ginseng, grape seed proanthocyanidin extract (GSPE), green tea, Hawthorne, lemon balm, milk thistle, oregano, peppermint, pomegranate juice, purslane, pycnogenol, red wine, rosemary, schizandra, wuweizi, wurenchun, trilinolein, sanchi, turmeric and combinations thereof.

The composition may further include an effective amount of at least one blood circulation promoter to provide increased blood circulation to an area to which the composition is applied (referred to herein as an "area of application"). The blood circulation promoter is selected from the group consisting of MSM, arnica extract, Roman chamomile oil, nettle extract, marigold extract, grape seed extract, blue-bottle extract, coriander oil, lime tree extract, marigold extract, feverfew extract, St. John's wort extract, witch hazel extract, arjuna, Bala, benzoin, bilberry, black pepper, blue gum eucalyptus, blue vervain, borneol, butcher's broom, cayenne, cypress, geranium, ginger, ginkgo, grape seed proanthocyanidin extract (GSPE), Hawthorne, L-arginine, lemon, lemon grass, linden flowers, niaouli, oat straw, orange blossom, passion flower, Peru balsam, pine, prickly ash bark, rose oils, rosemary, Spanish sage, spruce, Tien Chi ginseng, thyme, violet, white birch, yohimbe and combinations thereof.

The composition may further include an effective amount of at least one compound having antidepressant/anti-anxiety/anti-stress activity to provide at least one of a relaxing effect and a calming effect. The antidepressant/anti-anxiety/anti-stress compound is selected from the group consisting of MSM, kava kava extract, Roman chamomile extract, feverfew extract, St. John's wort extract, bee pollen, bergamot, black cohosh, black horehound, bugleweed, California poppy, clary sage, cowslip, damiana, DHEA, geranium, ginseng, gotu kola, grapefruit, hyssop, Jamaican dogwood, lady's slipper, lavender, lemon balm, licorice, linden, lobelia, mate, mistletoe, motherwort, mugwort, oat straw, passion flower, peppermint, rosemary, skullcap, valerian root, vervain, wild lettuce, wood betony and combinations thereof.

The following discussion describes ranges, preferred concentrations and optimum concentrations for preferred compositions according to one embodiment of the present invention. However, it is to be understood that the present invention is not limited to such embodiment, and other embodiments based on the disclosure presented herein will be readily apparent to one of ordinary skill in the art.

In one embodiment of the present invention, the composition contains whole leaf aloe vera concentrate. Aloe has been used for centuries to soothe and heal wounds, ulcers and burns. Aloe reduces inflammation, decreases swelling and redness, and accelerates wound healing. Aloe can also aid in keeping the skin supple, and has been used in the control of acne and eczema. It can relieve itching due to insect bites and allergies. Aloe's healing power comes from increasing the availability of oxygen to the skin, and by increasing the synthesis and strength of tissue.

Whole leaf aloe vera concentrate can comprise from about 55% to about 70% of the composition. Preferably, whole leaf aloe vera concentrate comprises from about 55% to about 65% of the composition. An optimum concentration of whole leaf aloe vera concentrate is about 60% of the composition.

In one embodiment of the present invention, the composition contains MSM (methyl-sulfonyl-methane or dimethyl sulfone). MSM is a natural and efficient source of sulfur that is used by many of the body's structural molecules, and MSM is metabolized sufficiently to supply the nutritional sulfur requirements of animals whose diet is deficient in assimilable sulfur due to the high percentage of processed foodstuffs consumed by today's society. U.S. Pat. Nos. 4,296,130, issued to Herschler on Oct. 20, 1981; and 4,477,469, issued to Herschler on Oct. 16, 1984, the Specifications of which are hereby expressly incorporated by reference in their entirety, disclose administration of preparations containing MSM to the skin, nails and other tissue and/or body fluids of a subject, while U.S. Pat. No. 4,973,605, issued to Herschler on Nov. 27, 1990, the Specification of which is hereby expressly incorporated herein by reference in its entirety, discloses oral or systemic administration of MSM for relief of pain and cramping. A variety of effects of MSM are listed in these patents, including providing relief from pain and stiffness; reducing swelling and inflammation; relieving leg and back cramps, muscle spasms and general soreness; reducing adverse response to inhalant allergens; controlling problems associated with gastric hyperacidity; providing relief from chronic constipation; reducing or eliminating hypersensitivity problems; providing relief from the symptoms of lung dysfunction; controlling parasitic infections associated with the intestinal or urogenital tracts; mood elevators; reduction in hypertension; and improving the overall health of domestic and farm animals whose caloric intake is predominantly or exclusively processed food rather than growing grasses and plants.

MSM can comprise from about 0.05% to about 15% of the composition of the present invention. Preferably, MSM comprises from about 0.1% to about 10% of the composition. An optimum concentration of MSM is about 5% of the composition.

In one embodiment of the present invention, the composition further comprises emu oil. Emu oil is obtained from a subcutaneous layer of fat found just under the skin on the back of an emu, a large, flightless Australian bird which is related to and resembles the ostrich. Emu oil, in one form or another, has been used for many years by the Aborigines of Australia to protect human skin from the adverse elements encountered in the Australian outback, as well as for treatment of arthritis and rheumatism, lumbago and joint stiffness. In addition, combinations of emu oil and a suitable transdermal transporter have been shown to exhibit anti-inflammatory activity in the cases of inflammatory arthritis and similar joint swelling diseases. Such work demonstrated that emu oil exhibits certain surface penetrating characteristics that, when the oil is combined with other compounds, increases the penetration of the compound as a whole.

Emu oil is generally comprised of myristic acid, palmitic acid, palmitoleic acid, margaric acid, stearic acid, elaidic acid, oleic acid, vaccenic acid, linoleic acid, linolenic acid, arachidic acid and eicosenoic acid. U.S. Pat. No. 6,103,246, issued to Tisdale et al on Aug. 15, 2000, the Specification of which is hereby expressly incorporated by reference in its entirety, discloses preparation of emu oil from an emu, as well as a composition which is a cream or lotion containing emu oil and at least one medically active component, such as lactic acid or some other alpha-hydroxy acid. The composition provides for increased penetrability due to the emu oil. In addition, U.S. Pat. Nos. 5,698,227, entitled "COMPOSITIONS COMPRISING LIDOCAINE AND EMU OIL AND METHODS OF USE THEREOF", issued to Daniel Rivlin on Dec. 16, 1997; and 5,849,334, entitled "COMPOSITION COMPRISING A LOCAL ANESTHETIC AND EMU OIL AND METHODS OF USE THEREOF", issued to Daniel Rivlin on Dec. 15, 1998, the Specifications of which are hereby expressly incorporated by reference in their entirety, describe compositions comprising emu oil and a local anesthetic such as lidocaine for topical application to achieve anesthesia of skin to which it is applied.

Emu oil can comprise from about 3% to about 7% of the composition. Preferably, emu oil comprises from about 4% to about 6% of the composition. An optimum concentration of emu oil is about 5% of the composition.

In one embodiment of the present invention, the composition further comprises arnica extract. The arnica plant has a bright yellow, daisy-like flower, and preparations made from the flowering heads have been used in homeopathic medicine for hundreds of years. The active components in arnica are sesquiterpene lactones, which are known to reduce inflammation and decrease pain. Arnica extract also stimulates the activity of white blood cells that perform much of the digestion of congested blood and disperse trapped, disorganized fluids from bumped and bruised tissue, joints and muscles. Arnica extract is known to stimulate blood circulation and can raise blood pressure, especially in the coronary arteries. It has anti-bacterial and anti-inflammatory qualities that can reduce pain and swelling, thereby improving wound healing.

Arnica extract can comprise from about 1% to about 10% of the composition. Preferably, Arnica extract comprises from about 3% to about 5% of the composition. An optimum concentration of arnica extract is about 4% of the composition.

The composition of the present invention further comprises glucosamine and chondroitin sulfate. Glucosamine is a naturally occurring amino sugar synthesized in the body from L-glutamine and glucose. Glucosamine has been used in several different forms for human supplementation, including glucosamine sulfate, glucosamine HCl, and N-acetyl glucosamine. Amino sugars are the key components of glycosaminoglycans and glycoproteins that allow cells in tissues to hold together, and are necessary for the construction and maintenance of virtually all connective tissues and lubricating fluids in the body. In particular, N-acetyl glucosamine and glucuronic acid are polymerized together to make the joint lubricant, hyaluronic acid.

Chondroitin sulfates provide the structural components of joint cartilage, inhibit free radical enzymes that degrade joint cartilage and collagen, and facilitate entry of glucosamine into inflamed joints. Like glucosamine, chondroitin sulfate attracts water into the cartilage matrix and stimulates the production of cartilage in addition to preventing enzymes from dissolving cartilage. It has been demonstrated that long-term treatment with chondroitin sulfate reduces pain and increases range of motion. In addition, chondroitin sulfate has recently been shown to have potent antioxidant activity in addition to possessing anti-inflammatory properties.

Glucosamine alone or in combination with chondroitin sulfate has been shown to have the ability to repair and improve joint function in addition to providing pain relief.

Glucosamine can comprise from about 0.01% to about 1% of the composition. Preferably, glucosamine comprises from about 0.05% to about 0.2% of the composition. An optimum concentration of glucosamine is about 0.1% of the composition.

Chondroitin sulfate can comprise from about 0.01% to about 1% of the composition. Preferably, chondroitin sulfate comprises from about 0.05% to about 0.2% of the composition. An optimum concentration of chondroitin sulfate is about 0.1% of the composition.

The composition of the present invention further includes at least one capsaicinoid. Capsaicinoids are analgesic and anti-neuralgic compounds that can be purified from capsicum oleoresin or cayenne. For reasons still not understood, capsaicinoids interfere with the action of substance P, a nerve chemical that sends pain messages to the brain. Capsaicins can be found in over-the-counter drugs that are recommended by doctors for arthritis, diabetic foot pain and the pain of shingles, and research also suggests that capsaicinoids can also help relieve cluster headaches. Capsaicinoids are also known to stimulate the blood and the heart, thereby increasing the pulse and regulating cholesterol and lipid levels.

The capsaicinoid may be at least one of capsaicin, nonivamide or combinations thereof. Alternatively, the capsaicinoid may be in the non-purified form of capsicum oleoresin or cayenne (*Capsicum annuum*).

When capsicum oleoresin is utilized as the capsaicinoid, capsicum oleoresin can comprise from about 0.01% to about 0.2% of the composition. Preferably, capsicum oleoresin comprises from about 0.05% to about 0.15% of the composition. An optimum concentration of capsicum oleoresin is about 0.1% of the composition. When one or more purified capsaicinoids are substituted for capsicum oleoresin, the concentration required will be less than that required for the unpurified capsicum oleoresin, and therefore the concentrations described herein for the capsicum oleoresin may be decreased.

The composition of the present invention may further include willow bark extract. Willow bark extract has been used throughout the world as an antipyretic, analgesic and anti-inflammatory. Willow bark contains salicylic acid and therefore is utilized as a natural substitute for aspirin (acetylsalicylic acid). Willow bark extract has been used to treat many different kinds of pain, including rheumatic pain, back pain, toothache, headache, menstrual cramps, sore throat, sore muscles, gout, angina, fever and headache associated with upper respiratory tract infections and influenza.

Willow bark extract can comprise from about 0.01% to about 10% of the composition. Preferably, willow bark extract comprises from about 0.05% to about 5% of the composition. An optimum concentration of willow bark extract is about 0.1% of the composition.

The composition of the present invention may further include witch hazel extract. Witch hazel extract is a strong astringent as well as an anti-inflammatory, and has also been shown to strengthen veins. Witch hazel extract has been used to treat eczema, hemorrhoids, injuries and wounds, skin ulcers, painful tumors, insect bites and varicose veins.

Witch hazel extract can comprise from about 0.01% to about 1% of the composition. Preferably, witch hazel extract comprises from about 0.05% to about 0.2% of the composition. An optimum concentration of witch hazel extract is about 0.1% of the composition.

The composition of the present invention may further include nettle extract. Nettle extract has been used for treatment of arthritis and allergy symptoms, as well as for treatment of hay fever, coughs, tuberculosis, kidney stones and urinary tract infections. Nettle extract has recently been found to contain a variety of active compounds such as cyclooxygenase and lipoxygenase inhibitors and substances that affect cytokine secretion.

In an open, randomized study, stinging nettle was given in combination with an anti-inflammatory drug and was shown to dramatically reduce the dose of anti-inflammatory drug needed for pain relief. Forty patients experiencing acute arthritis exacerbations took part in the study, with half receiving 200 mg standard dose of the prescription drug DICLOFENAC®, and the other half receiving 50 mg of DICLOFENAC® and 50 g of stewed nettle leaf. The combination of one-fourth the normal dose of DICLOFENAC® and nettle leaf was just as effective in relieving pain as the full dose of the drug alone. In a separate study, consumption of a dried powdered extract of nettle leaf was associated with a 50% reduction in dosage of a non-steroidal anti-inflammatory drug (NSAID).

Nettle extract can comprise from about 0.01% to about 1% of the composition. Preferably, nettle extract comprises from about 0.05% to about 0.2% of the composition. An optimum concentration of nettle extract is about 0.1% of the composition.

The composition of the present invention may further include coriander oil. Coriander oil is an essential oil steam distilled from the crushed seeds of the coriander plant. Coriander oil has a sweet and slightly musky, spicy, and woody aroma. It is warming, relaxing & stimulating, and because of its soothing properties, coriander oil is used to relieve stiffness, backache, pains and sprains and muscle ache.

Coriander oil's analgesic and tonic properties make it suitable for headaches and neuralgia. It is good for arthritis and rheumatism and is used to relieve diarrhea, flatulence, nausea, painful spasms, indigestion, and influenza. It also stimulates appetite in cases of anorexia and fatigue, enhances circulation and is used for hemorrhoids, poor circulation, and fluid retention. In addition to its analgesic and antineuralgic properties, coriander oil also exhibits antiseptic, antibacterial, antiviral, and antioxidant activities.

Coriander oil can comprise from about 0.01% to about 1% of the composition. Preferably, coriander oil comprises from about 0.05% to about 0.2% of the composition. An optimum concentration of coriander oil is about 0.1% of the composition.

The composition of the present invention may further include kava kava extract. Kava kava extract has been used for centuries in the South Pacific Island communities for its ability to relax the body both physically and mentally. Kava kava is a member of the pepper family and contains compounds called kavalactones that appear to improve well-being and relaxation without interfering with mental clarity and focus. Kava kava extract is used primarily to alleviate anxiety, depression and insomnia. In smaller doses it has a calming effect without slowing energy or thinking; in larger doses, it acts as a sedative without having any undesirable side effects. Kava kava extract also acts as a local anesthetic and relieves pain, and is also effective in reducing menstrual cramps.

Kava kava extract can comprise from about 0.01% to about 1% of the composition. Preferably, kava kava extract comprises from about 0.05% to about 0.2% of the composition. An optimum concentration of kava kava extract is about 0.1% of the composition.

The composition of the present invention may further include menthol. Menthol is a crystalline, organic compound of the isoprenoid family. It has a strong, minty, cooling odor and taste. It is obtained from peppermint oil or other mint oils. Menthol has local analgesic and counterirritant qualities and has been used topically for relief of muscle aches and sprains and similar conditions.

Menthol can comprise from about 0.01% to about 1% of the composition. Preferably, menthol comprises from about 0.05% to about 0.2% of the composition. An optimum concentration of menthol is about 0.1% of the composition.

The present invention further comprises Vitamin C in the form of ascorbyl palmitate. Vitamin C is involved in building and maintaining tissues and fortifying the immune system. It is known to be a potent antioxidant, as well as being toxic to viruses, bacteria and malignant tumor cells. Ascorbyl palmitate is the preferred form of vitamin C utilized in the composition of the present invention. Other forms of vitamin C, such as ascorbic acid and ascorbates, will change the color of the composition, whereas ascorbyl palmitate will not have this undesired effect.

Ascorbyl palmitate can comprise from about 0.03% to about 0.1% of the composition. Preferably, ascorbyl palmitate comprises from about 0.04% to about 0.07% of the composition. An optimum concentration of ascorbyl palmitate is about 0.05% of the composition.

The composition of the present invention may further include other herbal extracts, such as blue-bottle, Roman chamomile, marigold, lime tree, feverfew, St. John's wort and combinations thereof. When present, this combination of other herbal extracts can comprise from about 0.01% to about 1% of the composition. Preferably, this combination of herbal extracts is from about 0.05% to about 0.2% of the composition. An optimum concentration of the combination of herbal extracts is about 0.1% of the composition.

Blue-bottle extract is obtained from the cornflower plant, and has been shown to have anti-inflammatory and blood circulation promotion effects. It has been used successfully in the treatment of bruises, scorpion bites, ulcers and sores.

Roman chamomile oil promotes healthy skin, immune system and digestive function. It is believed to have analgesic, antidepressant, anti-inflammatory, anti-convulsive, antineuralgic; antiseptic, antispasmodic, anti-allergic, diuretic and sedative properties. Roman chamomile oil has been used for stress, sleeplessness, headaches, rashes, insect bites, toothache and menstrual or menopausal problems.

Calendula or marigold has been used since the time of the Greeks as a skin balm and anti-inflammatory. It is commonly used for skin conditions including minor abrasions and burns, conjunctivitis, aphthous stomatitis, pharyngitis, hemorrhoids, diaper rashes and ulcers. Marigold has also been used as a sedative and has been shown to have antiviral, antibacterial and antifungal properties. In addition, marigold has been shown to increase blood circulation and to aid in healing blood stagnation bruises. Experimental in vivo research suggests that marigold gently stimulates the immune system and promotes lymphatic drainage as well as reducing inflammation and pain.

Lime tree extract reduces tension in the muscle layer of the blood vessels, improves blood circulation, and helps heal damaged capillaries. In addition, lime tree extract contains an essential oil known as farnesol, which is similar to aloe and chamomile in its ability to act as a skin emollient.

Feverfew, as known as bachelor's button, has a long history of use as a treatment for disorders often controlled by aspirin, such as fever, headaches and some of the accompanying symptoms such as nausea and depression, as well as joint pain, stomach aches and menstrual pain. Feverfew has recently been shown to be an effective treatment for migraine headaches, and may also help ease diseases caused by chronic inflammation such as arthritis. The active ingredients in feverfew are sesquiterpene lactones. Feverfew inhibits the release of two inflammatory substances, serotonin and prostaglandins, and by inhibiting these amines as well as the production of histamine, the herb controls inflammation that constricts blood vessels in the head, and prevents blood vessel spasms which may contribute to headaches. Feverfew also relaxes smooth muscles in the uterus, promoting menstrual flow and inhibiting excessive blood clotting. In addition, feverfew may be effective in treating asthma and skin rashes.

St. John's wort, or Hypericum, has been used to treat many ailments, including cuts, grazes, bruises, minor burns, sciatica, injured nerves, inflammations, ulcers, poisonous reptile bites, kidney and lung ailments, allergic reactions, anxiety and depression. US clinical studies have shown that St. John's wort was just as effective in the treatment of mild-to-moderate depression as the antidepressant drugs to which it was compared (including PROZAC®) without the troubling side effects. It also has analgesic, anti-inflammatory and antidepressant properties, as well as being a superior moisturizer. Recent research suggests that St. John's wort has potential in the treatment of premenstrual syndrome, obsessive compulsive disorder and menopause symptoms. Laboratory studies suggest that the antidepressant effects of St. John's wort are similar to those of the antidepressant drugs called MAO inhibitors, and that it may work by interfering with the way the brain utilizes the neurotransmitter serotonin. In addition, St. John's wort is also a good source of antioxidants: with 11.7% of its content being bioflavonoids such as rutin, hyperin, quercetin and quercitrin, St. John's wort is one of the most concentrated herb sources of antioxidants.

In addition, the composition of the present invention is not limited to containing the herbal extracts described in detail herein previously. Rather, the composition of the present invention may comprise any pain relieving, anti-inflammatory, antioxidant, blood circulation promoter, or anti-depressant/anti-anxiety/anti-stress type of herb known to one of ordinary skill in the art, such as, but not limited to, arjuna, Bala, barley grass, bee pollen, benzoin, bergamot, bilberry, black cohosh, black horehound, black pepper, blue gum eucalyptus, blue vervain, borage, borneol, Boswellia, bromelain, bugleweed, bupleurem, burdock, butcher's broom, California poppy, camphor, cayenne, clary sage, cocash weed, cowslip, coughweed, cypress, damiana, dandelion, devil's claw root, DHEA (dehydroepiandosterone), Echinacea, elderflower, evening primrose oil, flaxseed, garlic, geranium, ginger, ginkgo, ginseng, golden groundsel, golden ragwort, golden Senecio, gotu kola, grapefruit, grape seed proanthocyanidin extract (GSPE), green tea, grundy swallow, Hawthorne, heather, hyssop, Jamaican dogwood, juniper, kaempferol, L-arginine, lady's slipper, lavender, lemon, lemon balm, lemon grass, licorice, life root, linden, lobelia, marjoram, mate, meadow sweet, milk thistle, mistletoe, motherwort, mugwort, NDGA, neem, niaouli, oat straw, orange blossom, oregano, Padma 28, passion flower, peppermint, Peru balsam, pine, pomegranate juice, prickly ash bark, purslane, pycnogenol, quercetin, ragwort, red wine, rose oils, rosemary, salicinum, schizandra, sharp sorrel, skullcap, Spanish sage, spruce, squaw weed, Tien Chi ginseng, thyme, trilinolein, turmeric, valerian root, vervain, violet, white birch, wild lettuce, wild yam, wintergreen, wood betony, wormwood, yohimbe, yucca, and the like. It is within the skill of a person of ordinary skill in the art to identify and determine an effective amount of one or more other herbal extracts that could be included in the composition of the present invention.

Arjuna is a famous cardiac tonic used in Ayurveda for a variety of heart conditions. Arjuna is used to lower blood pressure and heart rate, and has traditionally been given to support circulation and oxygenation of all tissues.

Bala is commonly used for heart disease and arthritic pain, and has shown to be helpful in soothing inflamed nerve tissue.

Barley grass contains over 3,000 live enzymes and is used for stomach and duodenal disorders, pancreatitis and as an anti-inflammatory substance. Numerous studies have shown that barley grass detoxifies, nutritionally supports the immune system and acts as an antioxidant.

Bee pollen contains lycopene carotenoid and is know to possess anti-depressant, anti-anxiety and anti-stress activity.

Bergamot is known to be calming, to promote restful sleep, to be mood uplifting, and to relieve anxiety, nervous tension and stress. Bergamot helps to provide mental clarity and alertness and sharpens the senses by refreshing and balancing the nervous system.

Bilberry contains compounds called anthocyanosides that provide antioxidant properties. Bilberry and its relatives blueberry, cranberry and huckleberry can aid is protecting the eyes in particular from free-radical damage.

Black cohosh, also known as black snakeroot, bugbane and squawroot, acts as a pain reliever and sedative. The root thereof has estrogenic properties and supplies estrogenic sterols which are the beginnings of steroid hormones such as estrogen, progesterone and testosterone. The chief constituent of black cohosh root is the amorphous resinous substance known as Cimicifugin, or Macrotin. Remifemin, the brand name of the standardized extract, has been used in Germany since the 1950s to treat menopausal symptoms. Black cohosh is most commonly used as a remedy for rheumatoid and myalgic pain and to control symptoms of menopause, premenstrual, mood swings, and dysmenorrhic neuronegative disorders, and as an alternative to common hormone replacement therapy.

Black horehound has sedative actions, and has been used as a remedy against hysteric and hypochondriac conditions.

Borage has been shown to have diaphoretic, expectorant, tonic, anti-inflammatory, diuretic, galactogogue and nervine activities. It has a reputation as an anti-inflammatory herb used in conditions such as pleurisy. Borage contains pyrrolizidine alkaloids, including lycopsamine, intermedine and their acetyl derivatives, amabiline and supinine.

Boswellia has been used for a variety of conditions, including arthritis, diarrhea, dysentery, pulmonary disease and ringworm. Studies have shown that Boswellia has an anti-inflammatory action much like the conventional non steroidal anti-inflammatory drugs (NSAIDs) used for inflammatory conditions. Boswellia inhibits pro-inflammatory mediators in the body, such as leukotrienes. And as opposed to NSAIDs, long-term use of Boswellia does not lead to irritation or ulceration of the stomach.

Bromelain is a general name for a family of sulfhydryl proteolytic enzymes obtained from the pineapple plant. Bromelain has been shown to have potent anti-inflammatory effects.

Bugleweed is a sedative, having mildly narcotic activities. Bugleweed has also been shown to be useful as an astringent.

Burdock is useful as part of a wider treatment for rheumatic complaints, especially when they are associated with psoriasis. Burdock seeds are crushed to make a popular tincture used to purify the blood, to treat gout and ulcers, arthritis and rheumatism.

Butcher's broom has been shown to increase circulation to help prevent post-operative thrombosis, phlebitis, varicose veins and hemorrhoids. Butcher's broom also strengthens blood vessels and helps to keep veins clean and healthy. Butcher's broom also helps to prevent blood clotting via its diuretic effect.

California poppy has the reputation of being a non-addictive alternative to the Opium poppy, although it is less powerful. It has been used as a sedative and hypnotic for children where there is over-excitability and sleeplessness. It can be used wherever an anti-spasmodic remedy is required.

The essential oil clary sage is used for its antidepressant, antiseptic, deodorant, digestive and sedative properties. It is estrogen-like, and can be used as an antispasmodic, relaxant, and detoxifier.

Cowslip is a sedative and antispasmodic. Cowslip has been utilized for strengthening the nerves and the brain, and for relieving restlessness and insomnia.

Damiana acts as a tonic on the central nervous system and the hormonal system. Damiana is used in treating depression and anxiety, particularly when influenced by sexual factors. Damiana contains a volatile oil containing pinene, cineol, cymol, arbutin (urinary antiseptic), cymene, cadinene, copaenen (useful in lung inflammation) and thymol, and also contains alkaloids, flavonoid, cyanogenic glycoside, tannins and resin.

The whole dandelion plant can be used to treat various ailments associated with joint inflammation due to gout or rheumatism, eczema, acne, warts, night blindness, mild hypertension, fever and congestion, liver and gall bladder, constipation and fluid retention. Active compounds found in dandelion leaves include bitter glycosides; lutein, violaxanthin and other carotenoids; terpenoids; choline; potassium salts; iron and other trace minerals; and vitamins A, B, C and D. Dandelion roots contain taraxacin; triterpines including taraxol and taraxasterol; sterols; inulin; sugars; pectin; glycosides; choline; phenolic acid; asparagine; volatile oils and vitamins. Dandelion flowers contain helenin and vitamins A and B-2 (riboflavin).

Devil's claw root has been used to treat arthritis, gout, rheumatism and spondylosis-induced lower back pain. Clinical study adds to the growing body of evidence supporting the use of devil's claw root in osteoarthritis: a double-blind, randomized trial concluded that devil's claw root was as effective in relieving pain as diacerhein (a type of drug known as a symptomatic slow-acting drug for osteoarthritis, or SYSDOA). Chantre et al, Phytomedicine 7:177 (2000).

DHEA (dehydroepiandosterone) has been shown to have therapeutic effects in many chronic conditions, including cardiovascular diseases, diabetes, hypercholesterolemia, obesity, multiple sclerosis, Parkinson's disease, Alzheimer's disease, disorders of the immune system, depression and osteoporosis. For each of these conditions listed above, there are many studies invariably demonstrating their association with low blood levels of DHEA.

Echinacea has been shown to have anti-inflammatory activity and is useful externally against inflammatory skin conditions including psoriasis and eczema. Echinacea also has antioxidant components and has also been shown to mobilize body reserves of vitamins A, E. and beta-carotene and thereby produce a stronger antioxidant effect in the body.

Elderflower has been used in herbal medicine to treat inflammation, arthritis, ear infections, coughs, and sore throats, and to reduce fever.

Flaxseed contains alpha-linolenic acid and lignans, and is the best food source of the essential fatty acid alpha-linolenic acid. Flaxseed has been shown to counter inflammation associated with gout, lupus and fibrocystic breasts. Flaxseed has also been used to treat acne, eczema, psoriasis, sunburn and rosacea.

The most active medicinal components of garlic are the sulfur-containing compounds, and the compound allicin is the major source of its antimicrobial action. Research with garlic has focused on four main areas: heart disease, cancer, infectious diseases and antioxidant effects. Garlic appears to have immune-stimulant, antioxidant and liver-protective benefits. Current anticancer research is focused on diallyl sulfides, breakdown products of allicin that are present in garlic oils.

Geranium has anti-inflammatory, antiseptic and hemostatic properties. Geranium can be used for sluggish, oily complexions and combination skin; menstrual problems, menopause and PMS; and hemorrhoids. Psychologically geranium has sedative, uplifting and anti-depressant properties and is often considered in times of depression, confusion, panic and anxiety. Geranium can also be useful in promoting concentration.

Ginger stimulates circulation in the GI tract and in other parts of the body. Ginger can also be used to relief of headaches, aches and pains, and as a cleansing agent through the kidneys and bowels. Ginger has been studied for its antibacterial, antifungal, pain-relieving, anti-ulcer and anti-tumor properties. Ginger has been shown to reduce the stickiness of blood platelets and may thereby reduce the risk of atherosclerosis. Limited studies also suggest ginger may reduce morning sickness and nausea after surgery. Ginger contains the antioxidant zingerone.

With hundreds of published scientific studies to document its complex and varied effects, ginkgo is among the world's most studied herbs. Millions of Americans and Europeans use ginkgo for memory, cognitive function, circulatory disorders and conditions of the eyes and ears. No other known circulation enhancer, natural or synthetic, can increase blood flow not only to healthy areas of the brain, but also to areas already damaged by disease. The wide-reaching benefits of ginkgo are thought to be largely due to its effects as an antioxidant. By preventing free radical damage, ginkgo appears to stabilize cell membranes and render blood vessel walls and red blood cells more flexible, thereby improving the flow of blood and thus oxygen to the brain, limbs and other areas supplied by capillaries, such as the eyes and ears. Ginkgo also helps support healthy circulation by inhibiting the effects of platelet activating factor (PAF), which causes blood clotting. Excess PAF has been linked to allergies, asthma, inflammatory conditions and cardiovascular diseases such as stroke. In addition, compounds isolated from ginkgo have been shown to have anti-arthritic, anti-inflammatory and analgesic activity.

Ginseng has been shown to reduce mental fatigue from mental stress and also increase tolerance of stress. Ginseng may also be effective for anxiety when it is stress-induced.

Gotu kola has been shown to have sedative, analgesic, antidepressant, antimicrobial, antiviral and immunomodulatory effects.

Grape seed proanthocyanidin extract (GSPE) demonstrates better antioxidant activity than other free radical scavengers. GSPE has been demonstrated to have significant antioxidant activity in liver and brain tissue and has been shown to decrease chemically-induced DNA damage, lipid peroxidation and production of oxygen free radicals. GSPE also provides better protection against oxidative damage than the same doses of other antioxidants, including vitamin C, vitamin E succinate and beta-carotene. GSPE appears to be better at scavenging free radicals and preventing oxidative damage to brain and liver tissue than other antioxidants. Results also show that GSPE is available to target tissues and therefore can be useful in vivo in inhibiting oxidative damage to brain and liver tissue. In addition, results from clinical trials with GSPE suggest that grape seed may help chronic venous insufficiency and its symptoms. GSPE may also be useful in the treatment of lymphedema, varicose veins, cancer, premenstrual syndrome, dental caries and circulatory disorders.

Green tea has well established antioxidant activity, and has been shown to contain polyphenols, compounds that have antioxidant capabilities greater than vitamins C and E. Green tea has also been linked to the prevention of stomach, colon, pancreatic, lung and breast cancers.

Hawthorne leaves and berries are both used in herbal supplements, since each is high in flavonoid content, which provides powerful antioxidant properties. Hawthorne has been used to treat heart disease and related symptoms, in addition to sleeplessness, nervousness, poor digestion and weight control.

Hyssop has anti-helminthic, anti-periodic, diaphoretic, emetic, expectorant, febrifuge, hemostatic, sedative, sudorific, tonic, tranquilizer and vermifuge properties. Hyssop has been used to treat albuminuria, the common cold, congestion, ear ailments, fever, gastrointestinal disturbances, insomnia, intestinal worms, nervous problems, sores, stomach ache, urinary ailments, viral infections and wounds.

Jamaican dogwood is a hypnotic sedative that exhibits nervine, anodyne and anti-spasmodic properties. Jamaican dogwood is a powerful remedy for the treatment of painful conditions such as neuralgia and migraine. Its main use is for insomnia.

Lady's slipper has sedative, mild hypnotic, spasmolytic, thymoleptic, diaphoretic and nervine properties. Lady's slipper is used in the treatment of all stress reactions, helping to elevate the mood, especially when there is depression. It is particularly of benefit in anxiety associated with insomnia. It can ease nervous pain, though it is best combined with other herbs for this purpose. It can also be helpful against cramps and muscle spasms and is useful as an aid to recovery from chronic conditions.

Lavender oil has applications as a stimulant, tonic, headache relief and for relief of intestinal gas. Lavender has also been used to quiet coughs and disinfect wounds. Applied as a compress, lavender oil provides relief from neuralgic pains, rheumatism, sprains and sore joints.

Lemon balm has mild sedative properties and has been used to relieve gas, reduce fever and increase perspiration. The volatile oil contains citral, citronellal, eugenol acetate and geraniol. Both oil and hot water extracts of the leaves of lemon balm have been shown to possess strong antibacterial and antiviral qualities.

Licorice contains active compounds that stimulate the secretion of aldosterone. Licorice can be as effective as and safer than codeine when used as a cough suppressant. Licorice has also been known to relieve rheumatism and arthritis.

Life root, also known as golden Senecio, squaw weed, golden groundsel, cocash weed, coughweed, ragwort, golden ragwort and grundy swallow, has been used as a uterine tonic, diuretic, expectorant, anti-inflammatory and emmenagogue. Life root has been used for many conditions of the reproductive organs of both males and females, especially when such conditions are accompanied with organ weakness and urinary tract symptoms. In particular, life root has been used to treat uterine prolapse, uterine congestion, and absent, painful or copius menstruation.

Linden is a well known relaxing remedy for nervous tension. Linden exhibits nervine, anti-spasmodic, hypotensive, diaphoretic, diuretic, anti-inflammatory, emmenagogue and astringent properties.

Lobelia contains the alkaloid lobeline and has been shown to act simultaneously as both a stimulant and relaxant. Lobelia has been used to treat asthma, cancer, chicken pox, convulsions, cough, gastrointestinal disturbances, gout, hemorrhoids, migraine, nausea, nicotinism, orthopedic ailments, pulmonary ailments, respiratory ailments, skin ailments, throat ailments, venereal ailments, vomiting and whooping cough.

Mate, also known as yerba mate, erva mate, Paraguay cayi, Paraguay tea and South American holly, has uses in treating mental and physical fatigue. Mate is also known to have analeptic, diuretic, inotropic, chronotropic, glycogenolytic and lipolytic effects. Mate has been used medicinally as a diuretic, tonic and a central nervous system stimulant. The primary active chemical constituency of mate is caffeine, theobromine, theophylline, saponins and chlorogenic acid.

Marjoram has been used since the time of the ancient Greeks for relaxation of muscles and to calm muscle spasms. Used in massage oil, compresses or in baths, marjoram is valuable in the treatment of arthritis, muscular pain and swelling. It is analgesic and warming, and for this reason, it can relieve dysmenorrhea.

Milk thistle has been shown to have positive effects in treating nearly every known form of liver disease, including cirrhosis, hepatitis, necroses, and liver damage due to drug and alcohol abuse. The active chemical component of the herb is silybin, which functions as an antioxidant and is one of the most potent liver protective agents known. Clinical trials have proven silybin to be effective in treating chronic liver diseases and in protecting the liver from toxic chemicals.

In small doses, mistletoe has nervine qualities and is used for the treatment of tension, insomnia and depression. In larger doses, mistletoe is used as a narcotic. Mistletoe is also used in treating arteriosclerosis, arthrosis, cancer, depression, epilepsy hypertension, insomnia and tension.

Motherwort is used as a sedative and can reduce muscle spasms, regulate blood pressure and rapid heartbeat and tone the heart. Motherwort has been shown to treat heart disease effectively by reducing cholesterol levels. Motherwort contracts the uterus after birth and helps calm anxious new mothers. Motherwort also treat menstrual irregularities and the symptoms of menopause.

Mugwort has many actions, including anti-helminthic, antiseptic, central nervous system depressant, diaphoretic, digestive, diuretic, expectorant, nervine, sedative and tonic. Mugwort has been used to treat hysteria, colic, common cold, dermatosis, dysmenorrhea, epilepsy, fever, nausea, neuralgia, orthopedic ailments, pulmonary ailments, scurvy, skin ailments, sores and venereal ailments.

Neem is considered one of the best healing and disinfectant agents for skin diseases. Neem is also used as an anti-inflammatory for joint and muscle pain.

Oat straw helps to strengthen the central nervous system and has been shown to increase blood circulation. Oat straw also aids in depression and the prevention of anxiety.

Oregano contains the potent antioxidant rosmarinic acid in addition to more than a dozen other antioxidants.

Padma 28 is an herbal combination used in traditional Tibetan medicine for anti-inflammatory and other effects. Padma 28 has been shown to cause a significant inhibition of inducible nitric oxide synthesis in tests utilizing a mouse macrophage cell line.

Passion flower has been shown to possess an analgesic activity as well as the ability to prevent, sleeplessness caused by brain inflammation, without side effects. Studies on induction of relaxation and sleep have shown that passion flower, unlike narcotics, induce sleep normally, with easy, light breathing and with little or no neural or mental depression, and upon awakening, patients show no signs of confusion, stupor or melancholy. Preparations of passion flower have been for nervous or easily aroused children, cardiovascular neurosis, bronchial asthma, coronary diseases, weak circulation, sleep disorders, problems of concentration in school children, and geriatrics.

Peppermint has been used in treating circulatory disorders, nervousness, insomnia, headaches, fevers, PMS, stress and tension. Externally, peppermint relieves itching and inflammation, and is also useful as a strong antiseptic. In addition, peppermint has recently been shown to be a powerful antioxidant.

Pomegranate juice has been shown to have potent anti-atherogenic effects, possibly due to its antioxidant activity.

Prickly ash bark is an excellent circulatory stimulant. Although it is slower working than cayenne, its effects are longer lasting. Prickly ash bark is also a blood purifier and is useful for skin diseases and accumulations in the joints.

Purslane is very rich in antioxidants, including vitamins A, C and E, as well as glutathione, an immune-system booster.

Red wine contains the compound resveratrol, which acts like an antibiotic to protect grapes from fungus, and may turn off a protein that guards cancer cells from cancer-fighting therapies such as chemotherapy. Resveratrol also blocks cell inflammation which is linked to arthritis and other diseases.

Rosemary has been shown to be endowed with the potent antioxidant rosmarinic acid, in addition to about a dozen other free radical scavengers. Rosemary is also used as a tonic for blood circulation and as a nerve tonic. Studies have shown that as well as being a stimulant to the nervous system, rosemary essential oil is primarily antiseptic and antibacterial. The warming and stimulating effects of rosemary help clear phlegm from the head and chest. In addition, a few drops of the essential oil in the bath restores energy levels after a period of prolonged stress. Rosemary is used to treat tension of nerves or stomach, dysplesia, colic, headache, depression, muscular pain, sciatica, neuralgia, premature baldness, menstrual problems, liver congestion and poor circulation.

Schizandra berries have been used by Chinese herbalists for centuries and are a great source of adaptogens, substances that help the body adjust to environmental conditions. Schizandra also contains antioxidant properties.

Skullcap has been used to treat nervous diseases, convulsions, neuralgia, insomnia, restlessness and even tetanus. In one study, skullcap was demonstrated to stabilize and normalize blood pressure. Skullcap is usually recommended for pain associated with nervous conditions, and may best be considered a mild neural sedative.

Trilinolein is a compound isolated from the Chinese herb sanchi and has been demonstrated to have concentration-dependent antioxidant effects. Trilinolein has been used to treat circulatory system disorders and has been shown to suppress cardiac arrythmias during ischemia and reperfusion and protected the hear muscle from injury due to ischemia.

Turmeric is a member of the ginger family and contains a variety of bioactive substances called curcuminoids. The most active component of turmeric is curcumin, which has been shown to anti-inflammatory activity that is comparable to steroidal and non steroidal drugs. Turmeric is also a potent antioxidant, and has been used to treat inflammatory conditions such as arthritis, muscle sprains and strains, and swelling due to various injuries, including surgery recovery and accidents. Research also suggests that turmeric may help to ward off certain kinds of cancers while promoting vascular health.

Valerian root has been used for thousands of years as a tranquilizer and calmative for several disorders such as restlessness, nervousness, insomnia, hysteria, menstrual problems, and as a sedative for a nervous stomach. Valerian root has marked sedative, anticonvulsive, hypotensive, tranquilizing, neurotropic, and anti-aggressive properties. The herb's primary functional effect is to suppress and regulate the autonomic nervous system. As a result, it has been found effective in treating psychosomatic diseases and childhood behavioral disorders that involve disregulation of the autonomic nervous system.

Vervain is used as a nervine to strengthen the nervous system while relaxing tension and stress. Vervain is also used as a poultice to treat wounds and sores, and can also be used as a mouthwash for mouth ulcers and gum disease.

Wild lettuce possesses sedative properties and is used to treat insomnia, restlessness and excitability (especially in children) and other manifestations of an overactive nervous system. As an anti-spasmodic, wild lettuce can be used as part of a holistic treatment of whooping cough, as well as dry, irritated coughs in general. It will relieve colic pains in the intestines and uterus and so may be used in dysmenorrhea. Wild lettuce also will ease muscular pains related to rheumatism and has been used as an aphrodisiac.

Wild yam has been used medicinally for rheumatic conditions, bilious colic, dysmenorrhea, nausea and menstrual cramps.

Wood betony has been shown to have mild analgesic, anti-diarrhetic, carminative, astringent and sedative properties. Wood betony has been used for heartburn, gout, nervousness, bladder and kidney stones, asthma and fatigue. Significant hypotensive activity has also been found in the constituents of wood betony, and it is also used to calm nerves, encourage sleep, and tone up glandular functioning.

Wormwood oil acts as a local anesthetic to relieve pains of rheumatism, neuralgia and arthritis. Wormwood is an anti-inflammatory herb that has been used for the treatment of rheumatism, cystitis, diarrhea, eczema, gastritis, impetigo and leukorrhea.

Yohimbe is an African herb that contains low levels of the alkaloid yohimbine. Yohimbine acts on peripheral blood vessels to further affect blood circulation.

Yucca contains saponins that block the release of toxins from the intestines which inhibit normal formation of cartilage. Yucca has been used to treat many forms of inflammation, including joint inflammations, osteoarthritis, rheumatoid arthritis, cancer and bleeding.

In addition, the composition of the present invention may include one or more EFAs (essential fatty acids). EFAs produce joint lubricants. Inflammatory disorders that are a direct result of clinical imbalances in fatty acid metabolism are associated with conditions such as cardiovascular disease, pregnancy, hyperactivity and rheumatoid arthritis. Examples of EFAs that may be utilized in accordance with the present invention include omega-3 and omega-6 fatty acids such as linolenic acid (LA) and alpha linolenic acid (LNA). In addition, any known herbs or various compounds that contain EFAs may be included in the composition of the present invention. Examples of such herbs that have been described herein previously include flaxseed and evening primrose oil.

Further, the composition of the present invention is not limited to containing vitamin C, and other vitamins having desired side effects, such as but not limited to, Vitamins A, D and E, may be included in the composition of the present invention. Also, a mixture of one or more vitamins may be included in the composition of the present invention. It is within the skill of a person of ordinary skill in the art to identify and determine an effective amount of one or more vitamins that could be included in the composition of the present invention.

In addition, one or more essential oils other than the essential oils previously described herein may be included in the composition of the present invention. Essential oils act as penetrating transdermal carriers that penetrate the skin the quickly and aid in transport of other components present in the composition of the present invention. Examples of essential oils that may be utilized in accordance with the present invention include: anise oil, apricot kernel oil, avocado oil, bergamot, balm mint oil, basil oil, bee balm oil, bergamot oil, birch oil, bitter almond oil, bitter orange oil, caraway oil, cardamom oil, cedarwood oil, cinnamon oil, clay oil, cloveleaf oil, clove oil, coconut oil, cypress oil, eucalyptus oil, evening primrose oil, fennel oil, gardenia oil, geranium oil, ginger oil, grapefruit oil, grape seed oil, hazelnut oil, hops oil, hyptis oil, indigo bush oil, jasmine oil, jojoba oil, juniper oil, kiwi oil, laurel oil, lavender oil, lemongrass oil, lemon oil, linden oil, lovage oil, matricaria oil, musk rose oil, neroli oil, nutmeg oil, olibanum, orange flower oil, orange oil, peach kernel oil, patchouli oil, pennyroyal oil, peppermint oil, pine oil, pine tar oil, rose hips oil, rosemary oil, rose oil, rue oil, sage oil, sambucus oil, sandalwood oil, sassafras oil, sesame oil, silver fir oil, spearmint oil, sweet almond oil, sweet marjoram oil, sweet violet oil, tar oil, tea tree oil, thyme oil, wheat germ oil, wild mint oil, yarrow oil, ylang ylang oil, and the like, as well as mixtures thereof.

The composition of the present invention may comprise one or more solvents. In one embodiment of the present invention, the composition includes water and SD-alcohol-40. Water can comprise from about 5% to about 40% of the composition. Preferably, water comprises from about 15% to about 25% of the composition. An optimum concentration of water is about 23% of the composition. SD-alcohol-40 can comprise from about 0.1% to about 10% of the composition. Preferably, SD-alcohol-40 comprises from about 0.5% to about 2% of the composition. An optimum concentration of SD-alcohol-40 is about 1% of the composition.

The pH of the composition of the present invention may be adjusted by an organic base, such as triethanolamine. Alternatively, an inorganic base such as sodium hydroxide may be used. Preferably, triethanolamine is used in the embodiment of the present invention.

Triethanolamine can comprise from about 0.05% to about 0.2% of the composition to adjust the pH. A preferred concentration of triethanolamine is from about 0.07% to about 0.15% of the composition. An optimum concentration of triethanolamine is about 0.1% of the composition.

The composition can further include a humectant. The humectant can comprise at least one compound selected from the group consisting of sorbitol, ethylene glycol, diethylene glycol, triethylene glycol, and other polyethylene glycols, propylene glycol, dipropylene glycol and other propylene glycols, 1,3-butylene glycol, 1,4-butylene glycol and other butylene glycols, glycerol, diglycerol and other polyglycerols, mannitol, xylitol, maltitol and other sugar alcohols, glycerol ethylene oxide (EO) and propylene oxide (PO) adducts, sugar alcohol EO and PO adducts, adducts of EO or PO and monosaccharides such as galactose and fructose, adducts of EO or PO and polysaccharides such as maltose and lactose, sodium pyrrolidonecarboxylate, and polyoxyethylene methyl glycoside (EO addition mols=10, 20, or the like). Preferably, the humectant is sorbitol.

The humectant can comprise from about 0.05% to about 1% of the composition. Preferably, the humectant comprises from about 0.1% to about 0.7% of the composition. An optimum concentration of humectant is about 0.7% of the composition.

The composition can further include a preservative component. The preservative component can comprise at least one preservative selected from the group consisting of grape seed extract, methylparaben, propylparaben, diazolindinyl urea and combinations thereof. Preferably, the preservative is grape seed extract.

The preservative can comprise from about 0.05% to about 0.20% of the composition. Preferably, the preservative comprises from about 0.07% to about 0.15% of the composition. An optimum concentration of preservative is about 0.1% of the composition.

The composition can further include a thickener, such as Carbomer-940. Carbomer-940 can comprise from about 0.05% to about 15% of the composition. Preferably, the thickener comprises from about 0.07% to about 10% of the composition. An optimum concentration of thickener is about 0.1% of the composition.

The composition can further include fragrance. Any type of natural or synthetic fragrance, such as floral, herbal or fruity fragrance could be utilized in accordance with the present invention. The use of fragrance is well known in the cosmetic art and in the art of over-the-counter drug formulation, and many suitable fragrances are known in the art. The stability and function of the cream is not altered by the presence or absence of fragrance.

Fragrance can comprise from about 0% to about 0.5% of the composition. Preferably, fragrance comprises from about 0.05% to about 0.25% of the composition. An optimum concentration of fragrance is about 0.1% of the composition. As indicated above, fragrance can be omitted, and it may be desirable to omit fragrance in circumstances in which the composition is intended for use on sensitive individuals or individuals who may undergo an allergic reaction to fragrance.

The composition may further include a colorant. Any type of natural or FD&C colorant, such as FD&C Blue No. 1, may be utilized in accordance with the present invention. Alternatively, the composition may be colorless, or possess a color provided by one or more of the compounds present therein.

A colorant can comprise from about 0% to about 0.5% of the composition. Preferably, the colorant comprises from about 0.05% to about 0.25% of the composition. An optimum concentration of colorant is about 0.1% of the composition. As indicated above, a colorant can be omitted, and it may be desirable to omit colorant in circumstances in which the composition is intended for use on sensitive individuals or individuals who may undergo an allergic reaction to colorant.

However, the composition of the present invention does not include hydroxy acids, surfactants or other softeners. Such compounds would break down the composition of the present invention and disrupt or destroy the inventive concept described herein.

EXAMPLES

Table I lists the ingredients of three compositions constructed in accordance with the present invention. The amount of each of the ingredients present in each composition is listed as weight percent of the composition. Each of the compositions is prepared as described herein below.

To prepare each of the three compositions of Table I, the water soluble ingredients listed for the desired example in Table I are combined and mixed together, and then the mixture is heated to a temperature in a range of from about 80° C. to about 85° C. In a separate container, the oil soluble ingredients listed for the desired examples in Table I are combined and mixed together, and then the mixture is heated to a temperature in a range of from about 80° C. to about 85° C. When both phases are at the same temperature, the phases are mixed together until the resulting composition is uniform, and then the resulting composition is cooled to room temperature.

Any of the compositions prepared as described herein above may be topically applied to a subject's skin for relief from a variety of symptoms, including pain, soreness, swelling and inflammation, caused by medical conditions or physical injuries. An amount of the composition is applied liberally to an area of discomfort on the subject by lightly rubbing the amount of composition into the skin in the area of discomfort, and the composition should cover at least the entire affected area. For example, the composition may be applied to the area of discomfort and to a portion of the area just outside of the affected area. Relief of at least one of the symptoms, that is, pain, soreness, redness, fever, swelling or inflammation, typically occurs within about 5 minutes to about 10 minutes. Application of the composition to the subject's skin should be repeated as needed for comfort. For example, the subject may reapply the composition as described above every about 10 minutes or longer, depending on the amount of time for which relief lasts.

It will be understood that the present invention is not limited to the examples presented herein but also includes variations of the embodiments disclosed herein apparent to one of ordinary skill in the art.

TABLE I

| INGREDIENT | Example I | Example II | Example III |
| --- | --- | --- | --- |
| Whole leaf Aloe Vera Concentrate | 60.0% | 60.0% | 60.0% |
| Purified Water | 23.05% | 17.99% | 16.94% |
| MSM | 5.0% | 0.10% | 10.0% |
| Emu Oil | 5.0% | 5.0% | 5.0% |
| Arnica Extract | 4.0% |  | 5.0% |
| SD-Alcohol-40 | 1.0% | 1.0% | 1.0% |
| Sorbitol | 0.70% | 0.10% | 0.70% |
| Menthol | 0.10% | 0.10% | 0.10% |
| Glucosamine HCl | 0.10% |  | 0.10% |
| Sodium Chondroitin Sulfate | 0.10% |  | 0.10% |
| Capsicum Oleoresin | 0.10% | 0.10% | 0.10% |
| Nettle Extract | 0.10% |  | 0.10% |
| Coriander Oil | 0.10% | 0.10% | 0.10% |
| Kava Kava Extract | 0.10% |  | 0.10% |
| Extracts of: Blue Bottle, Roman Chamomile, Marigold, Lime Tree | 0.10% |  | 0.10% |
| Extracts of: Blue Bottle, Roman Chamomile, Fever Few, St. John's Wort, Marigold, Lime Tree |  | 0.10% |  |
| Willow Bark Extract | 0.10% | 5.0% | 0.10% |
| Witch Hazel Extract | 0.10% | 0.10% | 0.10% |
| Carbomer-940 | 0.10% | 10.0% | 0.10% |
| Triethanolamine | 0.10% | 0.10% | 0.10% |
| Ascorbyl Palmitate | 0.05% |  | 0.05% |
| Grape Seed Extract |  | 0.10% |  |
| Fragrance |  | 0.10% | 0.10% |
| FD&C Blue No. 1 |  | 0.01% | 0.01% |

From the above description, it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A composition for topical application to an animal's skin for relief from a variety of symptoms caused by medical conditions or physical injuries, the composition consisting of:

an effective amount of at least one compound having analgesic activity to provide relief from at least one of pain, soreness and discomfort, the analgesic compound selected from the group consisting of *aloe vera*, MSM, emu oil, menthol, glucosamine, chondroitin, a capsaicinoid, arnica extract, coriander oil, Roman chamomile oil, willow bark extract, feverfew extract, St. John's wort extract, kava kava extract, nettle leaf, acetylsalicylic acid, Bala, black cohosh, black snakeroot, bugbane, squawroot, bupleurum, calendula, camphor, cayenne, devil's claw root, evening primrose oil, ginger, gotu kola, gingkgo, juniper, lavender oil, licorice, marjoram, meadow sweet, passion flower, quercetin, salicinum, wild yam, wintergreen, wood betony, wormwood and combinations thereof;

an effective amount of at least one compound having anti-inflammatory activity to provide relief from at least one of swelling, redness, fever and inflammation, the anti-inflammatory compound selected from the group consisting of *aloe vera*, MSM, emu oil, chondroitin, glucosamine, a capsaicinoid, arnica extract, grape seed extract, coriander oil, marigold extract, nettle leaf extract, Roman chamomile oil, blue-bottle extract, St. John's wort, willow bark extract, witch hazel extract, feverfew extract, barley grass, black cohosh, black snakeroot, bugbane, squawroot, Boswellia, borage, bromelain, burdock, calendula, cayenne, dandelion, devil's claw root, DHEA (dehydroepiandosterone), Echinacea, EFAs (essential fatty acids), omega-3 and omega-6 fatty acids including linoleic acid (LA) and alpha linolenic acid (LNA), elderflower, evening primrose oil, flaxseed, ginkgo, ginger, ginseng, Hawthorne, kaempferol, licorice, life root, golden Senecio, squaw weed, golden groundsel, cocash weed, coughweed, ragwort, golden ragwort, grundy swallow, linden, marjoram, meadow sweet, NDGA, neem, Padma 28, quercetin, turmeric, wild yam, wormwood, yucca and combinations thereof;

an effective amount of at least one compound having antioxidant activity to prevent damage or deterioration of tissue, the antioxidant compound selected from the group consisting of chondroitin, vitamin C, grape seed extract, St. John's wort extract, coriander oil, barley grass, bilberry, Echinacea, garlic, ginger, ginkgo, ginseng, grape seed proanthocyanidin extract (GSPE), green tea, Hawthorne, lemon balm, milk thistle, oregano, peppermint, pomegranate juice, purslane, pycnogenol, red wine, rosemary, schizandra, wuweizi, wurenchun, trilinolein, sanchi, turmeric and combinations thereof;

an effective amount of at least one compound having anti-neuralgic activity to provide relief of pain or discomfort along a course of a nerve or in an area of distribution of the nerve, the anti-neuralgic compound selected from the group consisting of at least one capsaicinoid, Roman chamomile oil, coriander oil and combinations thereof;

an effective amount of at least one compound having blood circulation promotion activity to increase blood circulation to an area of application, the blood circulation promotion compound selected from the group consisting of MSM, arnica extract, Roman chamomile oil, nettle extract, marigold extract, grape seed extract, blue-bottle extract, coriander oil, lime tree extract, marigold extract, feverfew extract, St. John's wort extract, witch hazel extract, arjuna, Bala, benzoin, bilberry, black pepper, blue gum eucalyptus, blue vervain, borneol, butcher's broom, cayenne, cypress, geranium, ginger, ginkgo, grape seed proanthocyanidin extract (GSPE), Hawthorne, L-arginine, lemon, lemon grass, linden flowers, niaouli, oat straw, orange blossom, passion flower, Peru balsam, pine, prickly ash bark, rose oils, rosemary, Spanish sage, spruce, Tien Chi ginseng, thyme, violet, white birch, yohimbe and combinations thereof;

an effective amount of at least one compound having antidepressant activity to provide at least one of a relaxing effect and a calming effect, the antidepressant compound selected from the group consisting of MSM, kava kava extract, Roman chamomile extract, feverfew extract, St. John's wort extract, bee pollen, bergamot, black cohosh, black horehound, bugleweed, California poppy, clary sage, cowslip, damiana, DHEA, geranium, ginseng, gotu kola, grapefruit, hyssop, Jamaican dogwood, lady's slipper, lavender, lemon balm, licorice, linden, lobelia, mate, mistletoe, motherwort, mugwort, oat straw, passion flower, peppermint, rosemary, skullcap, valerian root, vervain, wild lettuce, wood betony and combinations thereof; and wherein the composition does not contain a fragrance or a colorant.

2. The composition of claim 1 wherein the composition further comprises a humectant selected from the group consisting of sorbitol, ethylene glycol, diethylene glycol, triethylene glycol, propylene glycol, dipropylene glycol and other propylene glycols, 1,3-butylene glycol, 1,4-butylene glycol, glycerol, mannitol, xylitol, maltitol, glycerol ethylene oxide (EO), propylene oxide (PO) adducts, and combinations thereof.

3. The composition of claim 1 wherein the composition further comprises Carbomer-940.

4. The composition of claim 1 wherein the composition further comprises a preservative selected from the group consisting of grape seed extract, methylparaben, propylparaben, diazolindinyl urea and combinations thereof.

5. A composition for topical application to an animal's skin for relief from a pain or discomfort caused by a medical condition or a physical injury, the composition consisting of:

from about 55 to about 70 weight percent whole leaf aloe vera concentrate;

from about 5 to about 40 weight percent purified water;

from about 0.05 to about 8 weight percent MSM;

from about 3 to about 7 weight percent emu oil;

from about 1 to about 10 weight percent arnica extract;

from about 0.1 to about 10 weight percent SD-alcohol-40;

from about 0.05 to 1 weight percent sorbitol;

from about 0.01 to about 1 weight percent menthol;

from about 0.01 to about 1 weight percent glucosamine;

from about 0.01 to about 1 weight percent chondroitin sulfate;

from about 0.01 to about 0.2 weight percent capsicum oleoresin;

from about 0.01 to about 1 weight percent nettle extract;

from about 0.01 to about 1 weight percent coriander oil;

from about 0.01 to about 1 weight percent kava kava extract;

from about 0.01 to about 10 weight percent willow bark extract;

from about 0.01 to about 1 weight percent witch hazel extract;

from about 0.05 to about 15 weight percent Carbomer-940;

from about 0.05 to about 0.2 weight percent triethanolamine;

from about 0.03 to about 0.1 weight percent ascorbyl palmitate; and from about 0.01 to about 1 weight percent of a combination of herbal extracts comprising blue-bottle, Roman chamomile, marigold and lime tree extracts.

6. A composition for topical application to an animal's skin for relief from a pain or discomfort caused by a medical condition or a physical injury, the composition consisting of:

from about 55 to about 65 weight percent whole leaf aloe vera concentrate;

from about 15 to about 25 weight percent purified water;

from about 0.1 to about 6 weight percent MSM;

from about 4 to about 6 weight percent emu oil;

from about 2 to about 4 weight percent arnica extract;

from about 0.5 to about 2 weight percent SD-alcohol-40;

from about 0.1 to 0.7 weight percent sorbitol;

from about 0.05 to about 0.2 weight percent menthol;

from about 0.05 to about 0.2 weight percent glucosamine;

from about 0.05 to about 0.2 weight percent chondroitin sulfate;

from about 0.05 to about 0.15 weight percent capsicum oleoresin;

from about 0.05 to about 0.2 weight percent nettle extract;

from about 0.05 to about 0.2 weight percent coriander oil;

from about 0.05 to about 0.2 weight percent kava kava extract;

from about 0.05 to about 5 weight percent willow bark extract;

from about 0.05 to about 0.2 weight percent witch hazel extract;

from about 0.07 to about 10 weight percent Carbomer-940;

from about 0.07 to about 0.15 weight percent triethanolamine;

from about 0.04 to about 0.07 weight percent ascorbyl palmitate; and from about 0.05 to about 0.2 weight percent of a combination of herbal extracts comprising blue-bottle, Roman chamomile, marigold and lime tree extracts.

7. A method for relieving pain or discomfort of a subject wherein the pain or discomfort is caused by a medical condition or a physical injury, the method comprising the steps of:

providing a composition consisting of:

an effective amount of at least one compound having analgesic activity to provide relief from at least one of pain, soreness and discomfort, the analgesic compound selected from the group consisting of *aloe vera*, MSM, emu oil, menthol, glucosamine, chondroitin, a capsaicinoid, arnica extract, coriander oil, Roman chamomile oil, willow bark extract, feverfew extract, St. John's wort extract, kava kava extract, nettle leaf, acetylsalicylic acid, Bala, black cohosh, black snakeroot, bugbane, squawroot, bupleurum, calendula, camphor, cayenne, devil's claw root, evening primrose oil, ginger, gotu kola, gingkgo, juniper, lavender oil, licorice, marjoram, meadow sweet, passion flower, quercetin, salicinum, wild yam, wintergreen, wood betony, wormwood and combinations thereof;

an effective amount of at least one compound having anti-inflammatory activity to provide relief from at least one of swelling, redness, fever and inflammation, the anti-inflammatory compound selected from the group consisting of *aloe vera*, MSM, emu oil, chondroitin, glucosamine, a capsaicinoid, arnica extract, grape seed extract, coriander oil, marigold extract, nettle leaf extract, Roman chamomile oil, blue-bottle extract, St. John's wort, willow bark extract, witch hazel extract, feverfew extract, barley grass, black cohosh, black snakeroot, bugbane, squawroot, Boswellia, borage, bromelain, burdock, calendula, cayenne, dandelion, devil's claw root, DHEA (dehydroepiandosterone), Echinacea, EFAs (essential fatty acids), omega-3 and omega-6 fatty acids including linoleic acid (LA) and alpha linolenic acid (LNA), elderflower, evening primrose oil, flaxseed, ginkgo, ginger, ginseng, Hawthorne, kaempferol, licorice, life root, golden Senecio, squaw weed, golden groundsel, cocash weed, coughweed, ragwort, golden ragwort, grundy swallow, linden, marjoram, meadow sweet, NDGA, neem, Padma 28, quercetin, turmeric, wild yam, wormwood, yucca and combinations thereof;

an effective amount of at least one compound having antioxidant activity to prevent damage or deterioration of tissue, the antioxidant compound selected from the group consisting of chondroitin, vitamin C, grape seed extract, St. John's wort extract, coriander oil, barley grass, bilberry, Echinacea, garlic, ginger, ginkgo, ginseng, grape seed proanthocyanidin extract (GSPE), green tea, Hawthorne, lemon balm, milk thistle, oregano, peppermint, pomegranate juice, purslane, pycnogenol, red wine, rosemary, schizandra, wuweizi, wurenchun, trilinolein, sanchi, turmeric and combinations thereof;

an effective amount of at least one compound having anti-neuralgic activity to provide relief of pain or discomfort along a course of a nerve or in an area of distribution of the nerve, the anti-neuralgic compound selected from the group consisting of at least one capsaicinoid, Roman chamomile oil, coriander oil and combinations thereof;

an effective amount of at least one compound having blood circulation promotion activity to increase blood circulation in an area of application, the blood circulation promotion compound selected from the group consisting of MSM, arnica extract, Roman chamomile oil, nettle extract, marigold extract, grape seed extract, blue-bottle extract, coriander oil, lime tree extract, marigold extract, feverfew extract, St. John's wort extract, witch hazel extract, arjuna, Bala, benzoin, bilberry, black pepper, blue gum eucalyptus, blue vervain, borneol, butcher's broom, cayenne, cypress, geranium, ginger, ginkgo, grape seed proanthocyanidin extract (GSPE), Hawthorne, L-arginine, lemon, lemon grass, linden flowers, niaouli, oat straw, orange blossom, passion flower, Peru balsam, pine, prickly ash bark, rose oils, rosemary, Spanish sage, spruce, Tien Chi ginseng, thyme, violet, white birch, yohimbe and combinations thereof;

an effective amount of at least one compound having antidepressant activity to provide at least one of a relaxing effect and a calming effect, the antidepressant compound selected from the group consisting of MSM, kava kava extract, Roman chamomile extract, feverfew extract, St. John's wort extract, bee pollen, bergamot, black cohosh, black horehound, bugleweed, California poppy, clary sage, cowslip, damiana, DHEA, geranium, ginseng, gotu kola, grapefruit, hyssop, Jamaican dogwood, lady's slipper, lavender, lemon balm, licorice, linden, lobelia, mate, mistletoe, motherwort, mugwort, oat straw, passion flower, peppermint, rosemary, skullcap, valerian root, vervain, wild lettuce, wood betony and combinations thereof; and wherein the composition does not contain a fragrance or a colorant; and applying the composition topically to the subject's skin in an amount effective to cover at least an area affected by the pain or discomfort caused by the medical condition or physical injury.

8. The method of claim 7 wherein, in the step of providing a composition, the composition further comprises a humectant selected from the group consisting of sorbitol, ethylene glycol, diethylene glycol, triethylene glycol, propylene glycol, dipropylene glycol and other propylene glycols, 1,3-butylene glycol, 1,4-butylene glycol, glycerol, mannitol, xylitol, maltitol, glycerol ethylene oxide (EO), propylene oxide (PO) adducts, and combinations thereof.

9. The method of claim 7 wherein, in the step of providing a composition, the composition further comprises Carbomer-940.

10. The method of claim 7 wherein, in the step of providing a composition, the composition further comprises a preservative selected from the group consisting of grape seed extract, methylparaben, propylparaben, diazolindinyl urea and combinations thereof.

11. A method for relieving pain or discomfort of a subject wherein the pain or discomfort is caused by a medical condition or a physical injury, the method comprising the steps of:

providing a composition consisting of:
from about 55 to about 70 weight percent whole leaf *aloe vera* concentrate;
from about 5 to about 40 weight percent purified water;
from about 0.05 to about 8 weight percent MSM;
from about 3 to about 7 weight percent emu oil;
from about 1 to about 10 weight percent arnica extract;
from about 0.1 to about 10 weight percent SD-alcohol-40;
from about 0.05 to 1 weight percent sorbitol;
from about 0.01 to about 1 weight percent menthol;
from about 0.01 to about 1 weight percent glucosamine;
from about 0.01 to about 1 weight percent chondroitin sulfate;
from about 0.01 to about 0.2 weight percent capsicum oleoresin;
from about 0.01 to about 1 weight percent nettle extract;
from about 0.01 to about 1 weight percent coriander oil;
from about 0.01 to about 1 weight percent kava kava extract;
from about 0.01 to about 10 weight percent willow bark extract;
from about 0.01 to about 1 weight percent witch hazel extract;
from about 0.05 to about 15 weight percent Carbomer-940;
from about 0.05 to about 0.2 weight percent triethanolamine;
from about 0.03 to about 0.1 weight percent ascorbyl palmitate; and
from about 0.01 to about 1 weight percent of a combination of herbal extracts comprising blue-bottle, Roman chamomile, marigold and lime tree extracts; and applying the composition topically to the subject's skin in an amount effective to cover at least an area affected by the pain or discomfort caused by the medical condition or physical injury.

12. A method for relieving pain or discomfort of a subject wherein the pain or discomfort is caused by a medical condition or a physical injury, the method comprising the steps of:

providing a composition consisting of:
from about 55 to about 65 weight percent whole leaf aloe vera concentrate;
from about 15 to about 25 weight percent purified water;
from about 0.1 to about 6 weight percent MSM;
from about 4 to about 6 weight percent emu oil;
from about 2 to about 4 weight percent arnica extract;
from about 0.5 to about 2 weight percent SD-alcohol-40;
from about 0.1 to 0.7 weight percent sorbitol;
from about 0.05 to about 0.2 weight percent menthol;
from about 0.05 to about 0.2 weight percent glucosamine;
from about 0.05 to about 0.2 weight percent chondroitin sulfate;
from about 0.05 to about 0.15 weight percent capsicum oleoresin;
from about 0.05 to about 0.2 weight percent nettle extract;
from about 0.05 to about 0.2 weight percent coriander oil;
from about 0.05 to about 0.2 weight percent kava kava extract;
from about 0.05 to about 5 weight percent willow bark extract;
from about 0.05 to about 0.2 weight percent witch hazel extract;
from about 0.07 to about 10 weight percent Carbomer-940;
from about 0.07 to about 0.15 weight percent triethanolamine;
from about 0.04 to about 0.07 weight percent ascorbyl palmitate; and
from about 0.05 to about 0.2 weight percent of a combination of herbal extracts comprising blue-bottle, Roman chamomile, marigold and lime tree extracts; and applying the composition topically to the subject's skin in an amount effective to cover at least an area affected by the pain or discomfort caused by the medical condition or physical injury.

* * * * *